US012761196B2

(12) United States Patent
Mou et al.

(10) Patent No.: US 12,761,196 B2
(45) Date of Patent: Oct. 13, 2026

(54) GAS DETECTION DEVICE

(71) Applicant: Microjet Technology Co., Ltd., Hsinchu (TW)

(72) Inventors: Hao-Jan Mou, Hsinchu (TW); Chin-Chuan Wu, Hsinchu (TW); Ching-Sung Lin, Hsinchu (TW); Wen-Yang Yang, Hsinchu (TW); Chi-Feng Huang, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 281 days.

(21) Appl. No.: 18/613,928

(22) Filed: Mar. 22, 2024

(65) Prior Publication Data

US 2024/0426731 A1 Dec. 26, 2024

(30) Foreign Application Priority Data

Jun. 20, 2023 (TW) ................................ 112123174

(51) Int. Cl.
*G01N 33/00* (2006.01)
*G01N 1/22* (2006.01)
(Continued)

(52) U.S. Cl.
CPC ........... *G01N 33/0009* (2013.01); *G01N 1/22* (2013.01); *G01N 15/06* (2013.01); *G01N 15/075* (2024.01);
(Continued)

(58) Field of Classification Search
CPC ...... G01N 33/0009; G01N 1/22; G01N 15/06; G01N 15/075; G01N 15/1456;
(Continued)

(56) References Cited

U.S. PATENT DOCUMENTS

2019/0178775 A1* 6/2019 Feng ..................... F04B 45/047
2019/0187035 A1* 6/2019 Mou ...................... G01N 15/06
(Continued)

FOREIGN PATENT DOCUMENTS

CN 106969791 A 7/2017
CN 211476176 U 9/2020
(Continued)

OTHER PUBLICATIONS

Extended European Search Report for European Application No. 24170480.8, dated Oct. 9, 2024.

*Primary Examiner* — Benjamin R Schmitt
(74) *Attorney, Agent, or Firm* — Birch, Stewart, Kolasch & Birch, LLP

(57) ABSTRACT

A gas detection device is disclosed and includes a housing, an external connector, a power converter, a control processing board, a networking module and a particle detection module. The external connector, the power converter, the control processing board, the networking module and the particle detection module are accommodated in the housing to form a thin and portable device that is easy to carry. Due to the external connector is plug-and-play, when it is plugged in an indoor power supply, the particle detection module activates to detect the suspended particles, and the temperature and humidity sensor activates to detect the temperature and humidity. The detected data information is transmitted to a cloud processing device through the IOT communication by the networking module. An air quality information is immediately transmitted to an indoor air pollution prevention system, and a clean and safe breathing gas state formed in the indoor space is achieved.

15 Claims, 22 Drawing Sheets

(51) Int. Cl.

*G01N 15/06* (2006.01)
*G01N 15/075* (2024.01)
*G01N 15/14* (2006.01)
*G01N 15/00* (2006.01)

(52) U.S. Cl.

CPC . *G01N 15/1456* (2013.01); *G01N 2015/0046* (2013.01); *G01N 2015/1486* (2013.01); *G01N 33/0047* (2013.01); *G01N 33/0063* (2013.01); *G01N 33/0068* (2024.05)

(58) Field of Classification Search

CPC ........... G01N 33/0047; G01N 33/0063; G01N 33/0068; G01N 2015/0046; G01N 2015/1486

See application file for complete search history.

(56) References Cited

U.S. PATENT DOCUMENTS

| | | | | |
|---|---|---|---|---|
| 2019/0331582 | A1 | 10/2019 | Mou et al. | |
| 2020/0173971 | A1 | 6/2020 | Mou et al. | |
| 2021/0172850 | A1 | 6/2021 | Mou et al. | |
| 2021/0190516 | A1* | 6/2021 | Ventimiglia | G07C 5/008 |
| 2022/0003654 | A1* | 1/2022 | Pariseau | G01N 15/1404 |

FOREIGN PATENT DOCUMENTS

| | | | | |
|---|---|---|---|---|
| JP | 62-22056 | A | 1/1987 | |
| JP | 5-87692 | U | 11/1993 | |
| JP | 8-220042 | A | 8/1996 | |
| JP | 2001-6811 | A | 1/2001 | |
| JP | 2005-93290 | A | 4/2005 | |
| JP | 2011-29129 | A | 2/2011 | |
| JP | 2011-249266 | A | 12/2011 | |
| JP | 2013-130540 | A | 7/2013 | |
| JP | 2019-109225 | A | 7/2019 | |
| JP | 2019-215315 | A | 12/2019 | |
| JP | 2021-165729 | A | 10/2021 | |
| TW | 202020818 | A | 6/2020 | |
| TW | 202113324 | A | 4/2021 | |
| TW | 202316750 | A | 4/2023 | |
| WO | WO-2022117511 | A1 * | 6/2022 | G01N 33/0075 |

* cited by examiner

GAS DETECTION DEVICE

CROSS-REFERENCE TO RELATED APPLICATION

This application claims priority to Taiwan Patent Application No. 112123174, filed on Jun. 20, 2023. The entire contents of the above-mentioned patent application are incorporated herein by reference for all purposes.

FIELD OF THE INVENTION

The present disclosure relates to a gas detection device, and more particularly to an extremely thin gas detection device applied to arrange in an indoor air pollution prevention system for detecting gas, and instantly transmitting an air quality information to the system, thereby the indoor space can be cleaned to a safe and breathable state.

BACKGROUND OF THE INVENTION

Suspended particles are solid particles or droplets contained in the air. Since the sizes of the suspended particles are really small, the suspended particles may enter the lungs of human body through the nasal hair in the nasal cavity easily, causing inflammation in the lungs, asthma or cardiovascular disease. If other pollutants are attached to the suspended particles, it will further increase the harm to the respiratory system. In recent years, the problem of air pollution is getting worse. In particular, the concentration of particle matters (e.g., PM2.5) is often too high. Therefore, the monitoring to the concentration of the gas suspended particles is taken seriously. However, the gas flows unstably due to variable wind direction and air volume, and the general gas-quality monitoring station is located in a fixed place. Under this circumstance, it is impossible for people to check the concentration of suspended particles in current environment.

Nowadays, people pay more and more attention to the air quality in the environment. Various of gases and substances, such as carbon monoxide, carbon dioxide, volatile organic compounds (VOC), Particulate Matter 2.5 (PM2.5), nitric oxide, sulfur monoxide, and so on, exposure in the ambient environment will cause human health problems or even is harmful to the life. Therefore, people pay more and more attention to the air quality in the environment in every country, and how to monitor and keep away from the harmful air quality become a currently concerned issue.

Generally, it is feasible to use a gas detection device to monitor the air quality in the environment. If the gas detection device is capable of providing people with the monitored information relating to the environment immediately for warning, it may help people to escape or prevent from the injuries and influence on human health caused by the exposure to the gases and substances described above in the ambient environment. In other words, gas detection device is suitable for monitoring the air in the ambient environment.

Therefore, there is a need of providing an extremely thin gas detection device applied to arrange in an indoor air pollution prevention system, which is plug-and-play for detecting the air in the ambient environment indoor, and instantly transmitting an air quality information to the system, thereby the indoor space can be cleaned to a safe and breathable state

SUMMARY OF THE INVENTION

One object of the present disclosure is to provide a gas detection device, wherein an external connector, a power converter, a control processing board, a networking module and a particle detection module are accommodated in the housing to form a thin and portable device that is easy to carry. Since the external connector is plug-and-play, when it is plugged in an indoor power supply, the particle detection module starts detecting the suspended particles (e.g., PM1, PM2.5, or PM10) in the gas and the temperature and humidity sensor starts detecting the temperature and humidity in the environment. The detected data information can be transmitted to a cloud processing device through the IOT communication by the networking module. The detected data information can not only be transmitted as warnings or notifications on the indoor display device, but also on the mobile device application (APP). In addition, the detected data information can be compared through intelligent comparison and big data comparison of the cloud processing device. Namely, the cloud processing device sends communication commands to the indoor gas cleaning and exchange filtering devices (such as purifiers, exhaust fans, range hoods, fresh air fans, etc.), so as to effectively remove the indoor air pollution. Consequently, the gas detection device is constructed for detecting gas in an indoor air pollution prevention system, and instantly transmits the air quality information to the system, so as to achieve a clean and safe breathing gas state.

In accordance with an aspect of the present disclosure, a gas detection device is provided. The gas detection device comprises a housing, an external connector, a power converter, a control processing board, a networking module and a particle detection module. The housing includes an upper housing and a lower housing, wherein a plurality of vents are arranged on an side edge of the lower housing, a lug hole is arranged on a lower side of the lower housing, and a recessed groove formed on a bottom surface of the lower housing. The external connector pivotally connects to the lower housing. When not in use, the external connector is folded and hidden in the recessed groove without protruding, when in use, the external connector is rotated out the recessed groove to expose out the lower case, and connects to an external power supply. The power converter electrically connects to the external connector, and converts the external power supply into a DC power. The control processing board electrically connects to the power converter for providing an activation power supply, and receiving and processing a plurality of data information to convert into a communication information. The networking module is disposed on a side of the upper housing, and is integrally packaged on the control processing board to form an integrated circuit. Also, the networking module receives and outputs the communication information processed by the control processing board. The particle detection module is disposed and positioned on the other side of the bottom surface of the lower housing, and is also adjacent to an opposite side of the networking module packaged on the control processing board. The particle detection module electrically connects to the control processing board through a first flexible band to detect gas and acquires the data information of the gas, and transmits the data information to the control processing board to convert into the communication information. In addition, the control processing board outputs the communication information through the networking module. The temperature and humidity sensor is disposed on a side of the lower housing, and electrically connects to the control processing board through a second flexible band for detecting temperature and humidity, and acquires the data information of the temperature and humidity. The data information of the temperature and humidity is transmitted to the control processing board to convert into the communication information, and the communication information is outputted through the networking module by the control processing board.

BRIEF DESCRIPTION OF THE DRAWINGS

The above contents of the present disclosure will become more readily apparent to those ordinarily skilled in the art after reviewing the following detailed description and accompanying drawings, in which.

DETAILED DESCRIPTION OF THE PREFERRED EMBODIMENT

Figure 1A:
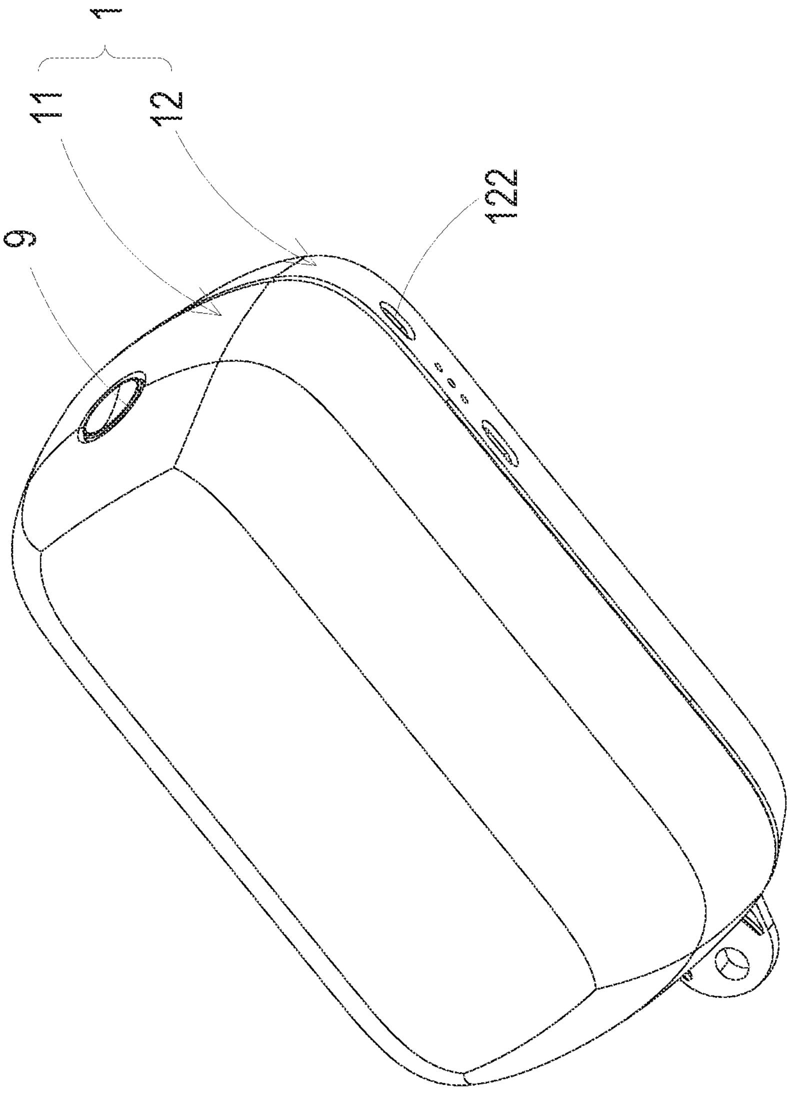
FIG. 1A is a schematic perspective view illustrating a gas detection device according to the embodiment of the present disclosure.

The present disclosure will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Please refer to FIG. 1A, FIG. 1B, FIG. 2A and FIG. 2B. The present disclosure provides a gas detection device, which includes a housing 1, an external connector 2, a power converter 3, a control processing board 4, a networking module 5, a particle detection module 6, and a temperature and humidity sensor 7.

Figure 1B:
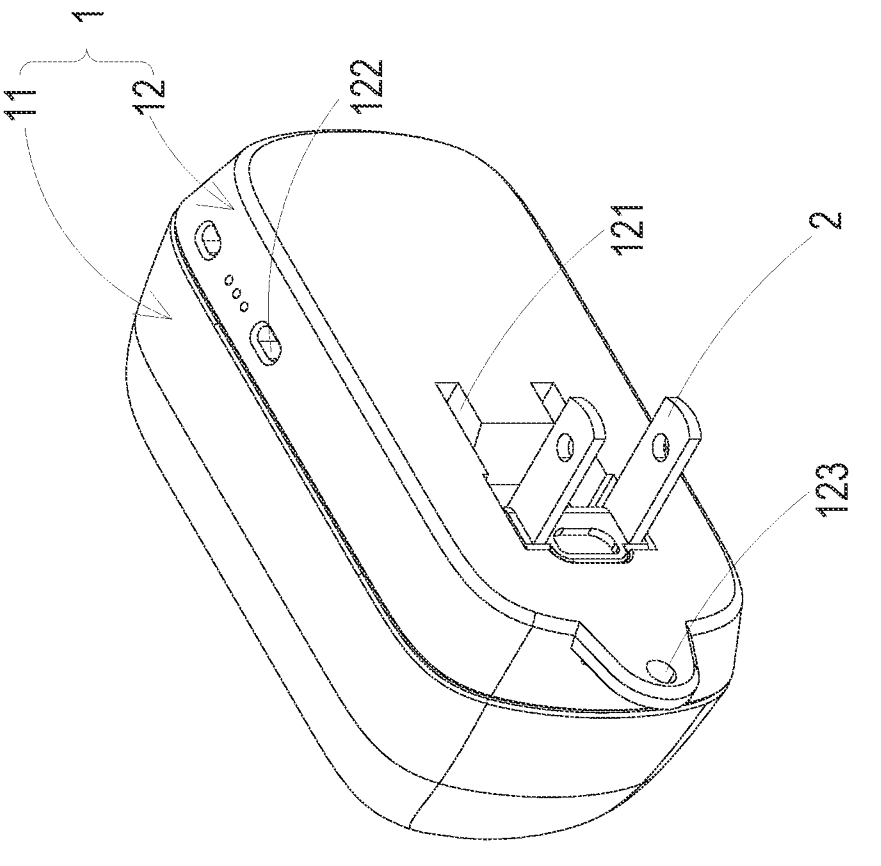
FIG. 1B is a schematic perspective view illustrating an external connector of the gas detection device in an open state according to the embodiment of the present disclosure.
Figure 1C:
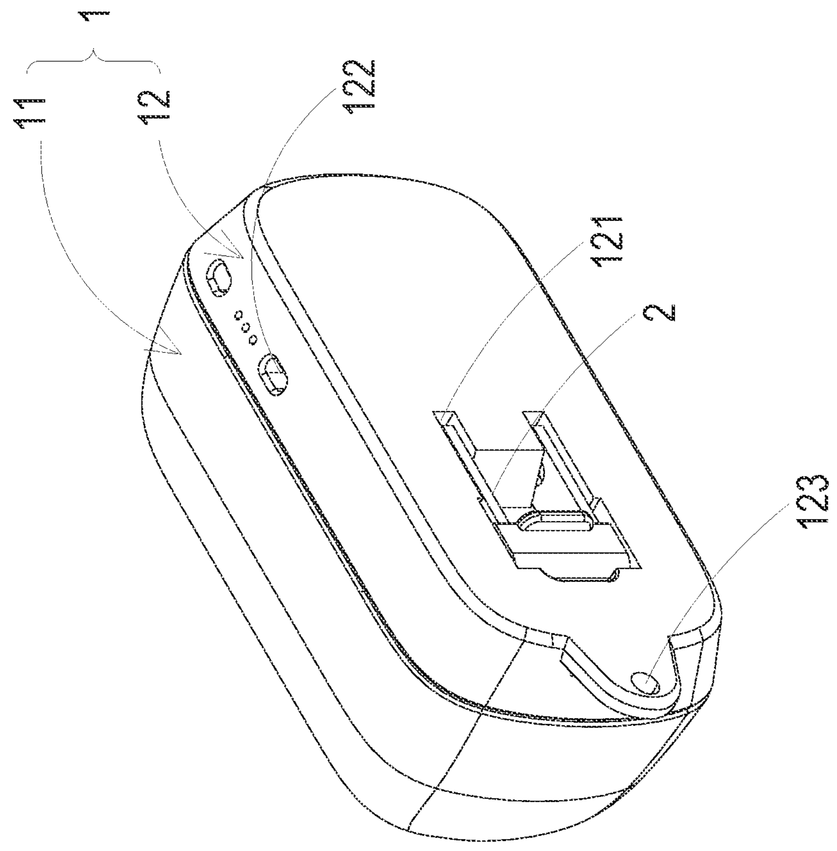
FIG. 1C is a schematic perspective view illustrating the external connector of the gas detection device in a close state according to the embodiment of the present disclosure.

In this embodiment, the above-mentioned housing 1 comprises an upper housing 11 and a lower housing 12, wherein the power converter 3, the control processing board 4, the networking module 5, the particle detection module 6, and the temperature and humidity sensor 7 are disposed between the upper housing 11 and the lower housing 12. Moreover, a plurality of vents 122 are arranged on an side edge of the lower housing 12 for introducing gas within the housing 1 or discharging gas outside the housing 1, a lug hole 123 is arranged on a lower side of the lower housing 12, and a recessed groove 121 is formed on a bottom surface of the lower housing 12. The external connector 2 pivotally connects to the lower housing 12. When not in use, the external connector 2 is folded and hidden in the recessed groove 121 without protruding (as shown in FIG. 1C), when in use, the external connector 2 is rotated out the recessed groove 121 to expose out the lower case 12 (as shown in FIG. 1B) and connect to an external power supply. Preferably but not exclusively, when the external connector 2 is plugged into the external power supply, a locking element (not shown) passes through the lug hole 123 and is locked into a socket (not shown), so as to position the entire gas detection device. In this circumstance, the gas detection device is positioned, and is not easy to be touched or tripped. Notably, the external connector 2 is one selected from the group consisting of a power connector, a USB port, a mini-USB port, a Micro-USB port and a Type-C USB port. In this embodiment, the external connector 2 as shown in FIG. 1B is a power connector. In the embodiment, the power converter 3 is electrically connected to the external connector 2, and converted the external power supply into a DC power. In some embodiments, the power converter 3 and the networking module 5 are integrally packaged on the control processing board 4 to form an integrated circuit. In addition, the control processing board 4 electrically connects to the power converter 3 for providing an activation power supply, and receives and processes a plurality of data information to convert into a communication information. The networking module 5 is disposed on the inner side of the upper housing 11 for receiving and outputting the communication information processed by the control processing board 4. The particle detection module 6 is disposed and positioned on the other side of the bottom surface of the lower housing 12, and is also adjacent to the opposite side of the networking module 5 packaged on the control processing board 4. In the embodiment, the particle detection module 6 electrically connects to the control processing board 4 through a first flexible band to detect gas and acquire the data information of the gas, transmits the data information to the control processing board 4 to convert into the communication information, and then, the control processing board 4 outputs the communication information through the networking module 5. The temperature and humidity sensor 7 is disposed on the side of the lower housing 12, which can be disposed in any position on the other side of the bottom surface of the lower housing 12, for example, the side edge or the lower side of the inner surface of the lower housing 12. In some embodiments, the temperature and humidity sensor 7 is disposed on the side edge of the inner surface of the lower housing 12, which is adjacent the particle detection module 6 and between the particle detection module 6 and the plurality of the vents 122. In addition, the temperature and humidity sensor 7 electrically connects to the control processing board 4 through a second flexible board for detecting temperature and humidity, and acquires the data information of the temperature and humidity, wherein the data information is transmitted to the control processing board 4 to convert into the communication information, and the communication information is outputted through the networking module 5 by the control processing board 4.

Figure 2A:
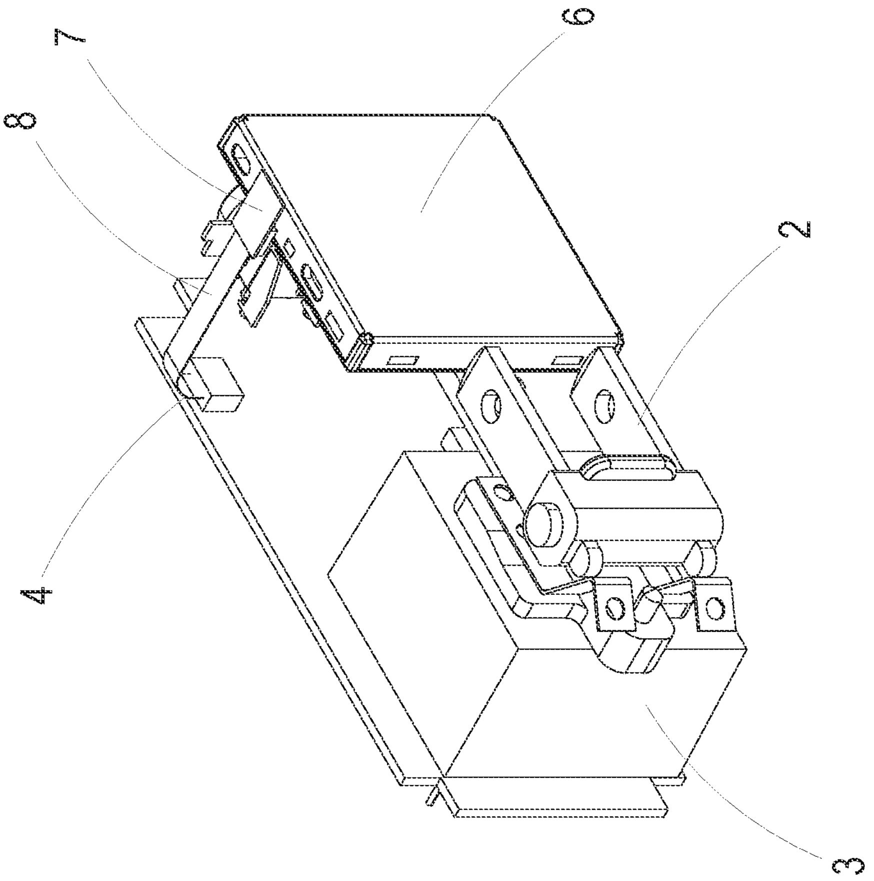
FIG. 2A is a schematic perspective view illustrating the internal relevant components of the gas detection device according to the embodiment of the present disclosure.
Figure 2B:
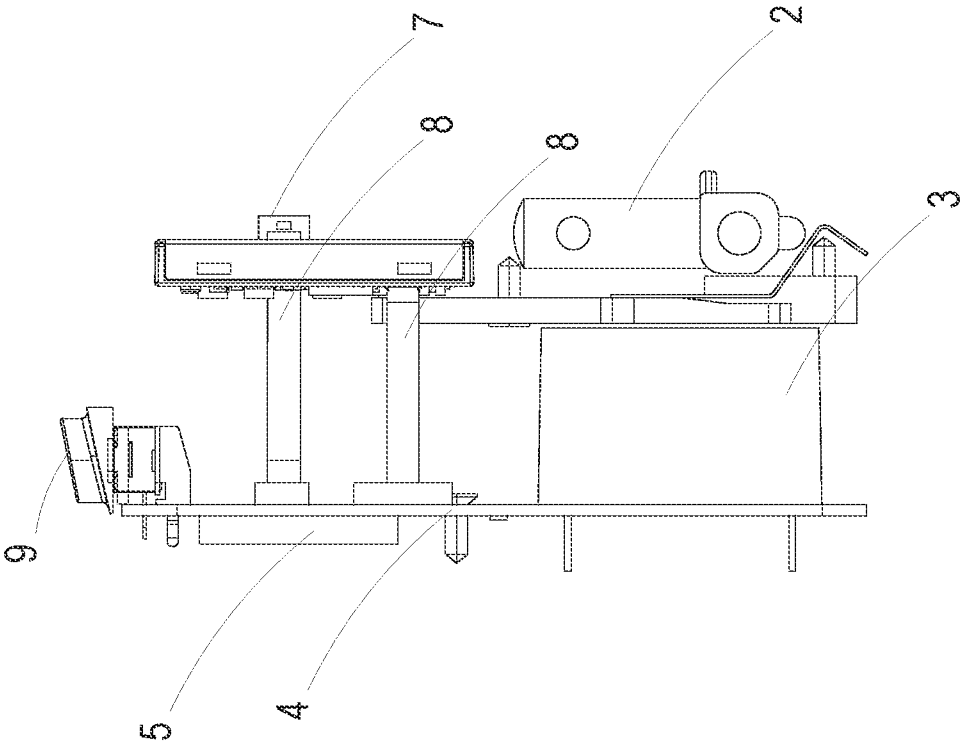
FIG. 2B is a schematic lateral view illustrating the internal relevant components of the gas detection device according to the embodiment of the present disclosure.

Please refer to FIG. 2A and FIG. 2B again. The external connector 2 connects to an external power supply, so as to provide power to the power the power converter 3. The power is converted into a DC power and transmitted to the control processing board 4 by the power converter, and then provided to the networking module 5, the particle detection module 6, and the temperature and humidity sensor 7 for use and activation. As shown in FIG. 2B, a person skilled in the art can easily understand that the flexible band is a transmission connection cable required for electrical connection of electronic components. For concise explanation, the following flexible band 8 can be a first flexible band, a second flexible band, etc., which are arranged to connect the particle detection module 6 and the temperature and humidity sensor 7, respectively. In the embodiment, the particle detection module 6 electrically connected to the control processing board 4 through the first flexible band, and the temperature and humidity sensor 7 is electrically connected to the control processing board 4 through the second flexible band. In addition, in the embodiment, the control processing board 4 also electrically connects to a switch 9. The switch 9 is exposed outside the upper housing 11 for the user to press, so that the control processing board 4 can supply the activation power supply to activate and control the operation of the networking module 5, the particle detection module 6 and the temperature and humidity sensor 7. In the embodiment, the networking module 5 is for activating the internet of things (IOT) communication, but not limited thereto. The particle detection module 6 is for detecting the suspended particles (e.g., PM1, PM2.5, or PM10) in the gas, but not limited thereto. The temperature and humidity sensor 7 is for detecting the temperature and humidity in the ambient environment. Notably, the networking module 5 is a WIFI communication module. In this embodiment, the networking module 5 is a cloud computing service wireless network communication module, such as Amazon Web Services (AWS), but not limited thereto. The networking module 5 is disposed on the side of the upper housing 11, which exposes outside the gas detection device. In this circumstance, it is easy to receive or send communication signals, and the networking module 5 is not easy to be shielded by the control processing board 4 and cause interference to the communication signals.

Please refer to FIG. 3A to FIG. 7B. In the embodiment, the above-mentioned particle detection module 6 includes a base 61, a piezoelectric actuator 62, a driving circuit board 63, a laser component 64, a particulate sensor 65, and an outer cover 66. In the embodiment, the driving circuit board 63 covers and is attached to a second surface 612 of the base 61, and the laser component 64 is positioned and disposed on the driving circuit board 63, and is electrically connected to the driving circuit board 63. The particulate sensor 65 is positioned and disposed on the driving circuit board 63, and is electrically connected to the driving circuit board 63. The outer cover 66 covers the base 61 and is attached to a first surface 611 of the base 61. Moreover, the outer cover 66 includes a side plate 661. The side plate 661 has an inlet opening 661*a* and an outlet opening 661*b*. When the outer cover 66 is disposed and positioned in the lower housing 12 of the housing 1, the inlet opening 661*a* introduces gas into the particle detection module 6 from the vents 122, and the outlet opening 661*b* outputs gas to the vents 122, so as to exhaust out the gas detection device.

Figure 4A:
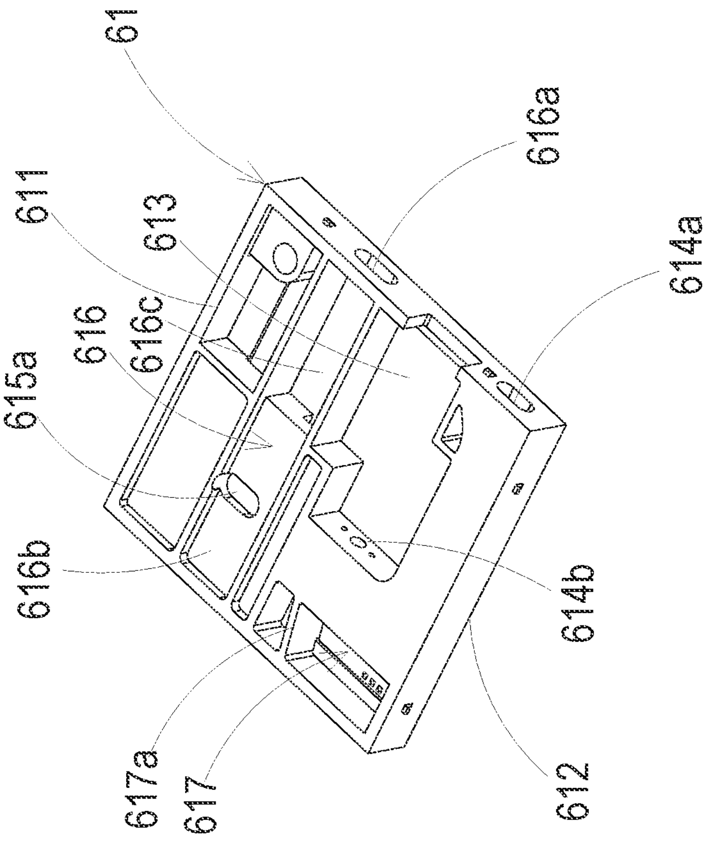
FIG. 4A is a schematic perspective view illustrating a base of the particle detection module according to the embodiment of the present disclosure.
Figure 4B:
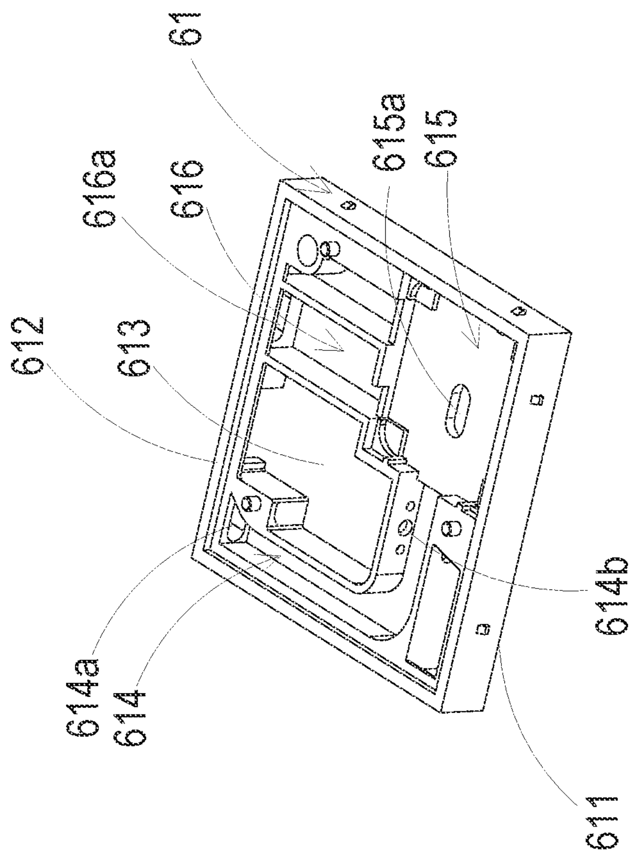
FIG. 4B is a schematic perspective view illustrating the base of the particle detection module according to the embodiment of the present disclosure and taken from another perspective angle.

As shown in FIGS. 4A and 4B. The base 61 includes a first surface 611, a second surface 62, a laser loading region 613, a gas-inlet groove 614, a gas-guiding-component loading region 615 and a gas-outlet groove 616. The first surface 611 and the second surface 612 are two surfaces opposite to each other. In the embodiment, the laser loading region 613 is hollowed out from the first surface 611 toward the second surface 612. The gas-inlet groove 614 is concavely formed from the second surface 612 and disposed adjacent to the laser loading region 613. The gas-inlet groove 614 includes a gas-inlet 614*a* and two lateral walls. The gas-inlet 614*a* is in communication with an environment outside the base 61, and is spatially corresponding in position to the inlet opening 661*a* of the outer cover 66. Two transparent windows 614*b* are opened on the two lateral walls of the gas-inlet groove 614 and are in communication with the laser loading region 613. Therefore, the first surface 611 of the base 61 is covered and attached by the outer cover 66, and the second surface 612 is covered and attached by the driving circuit board 63, so that an inlet path is defined by the gas-inlet groove 614.

In the embodiment, the above-mentioned gas-guiding-component loading region 615 is concavely formed from the second surface 612 and in communication with the gas-inlet groove 614. A ventilation hole 615*a* penetrates a bottom surface of the gas-guiding-component loading region 615. In the embodiment, the gas-outlet groove 616 includes a gas-outlet 616*a*, and the gas-outlet 616*a* is spatially corresponding to the outlet opening 661*b* of the outer cover 66. The gas-outlet groove 616 includes a first section 616*b* and a second section 616*c*. The first section 616*b* is concavely formed out from the first surface 611 in a region spatially corresponding to a vertical projection area of the gas-guiding-component loading region 615. The second section 616*c* is hollowed out from the first surface 611 to the second surface 612 in a region where the first surface 611 is extended from the vertical projection area of the gas-guiding-component loading region 615. The first section 616*b* and the second section 616*c* are connected to form a stepped structure. Moreover, the first section 616*b* of the gas-outlet groove 616 is in communication with the ventilation hole 615*a* of the gas-guiding-component loading region 615, and the second section 616*c* of the gas-outlet groove 616 is in communication with the gas-outlet 616*a*. In that, when first surface 611 of the base 61 is attached and covered by the outer cover 66 and the second surface 612 of the base 61 is attached and covered by the driving circuit board 63, the gas-outlet groove 616 and the driving circuit board 63 collaboratively define an outlet path.

Figure 5:
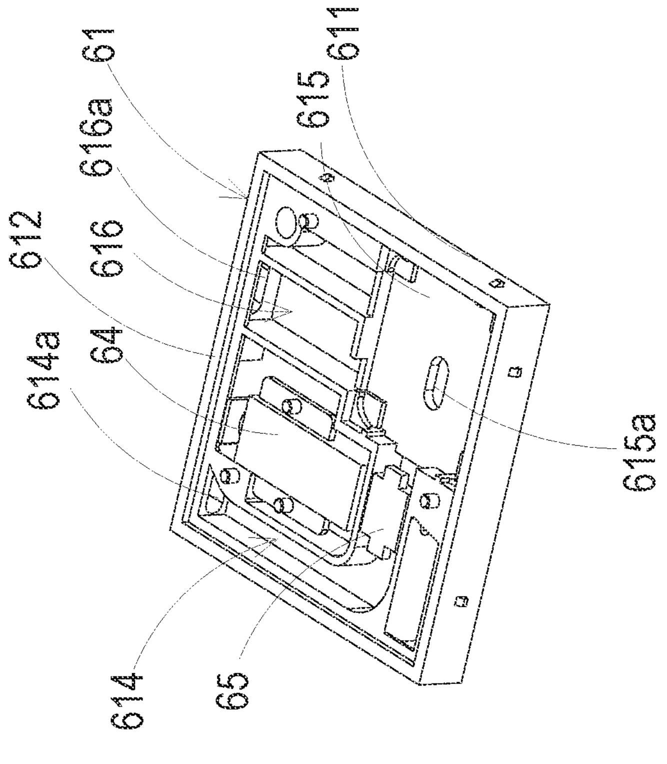
FIG. 5 is a schematic perspective view illustrating a laser component and a particulate sensor accommodated in the base according to the embodiment of the present disclosure.
Figure 6A:
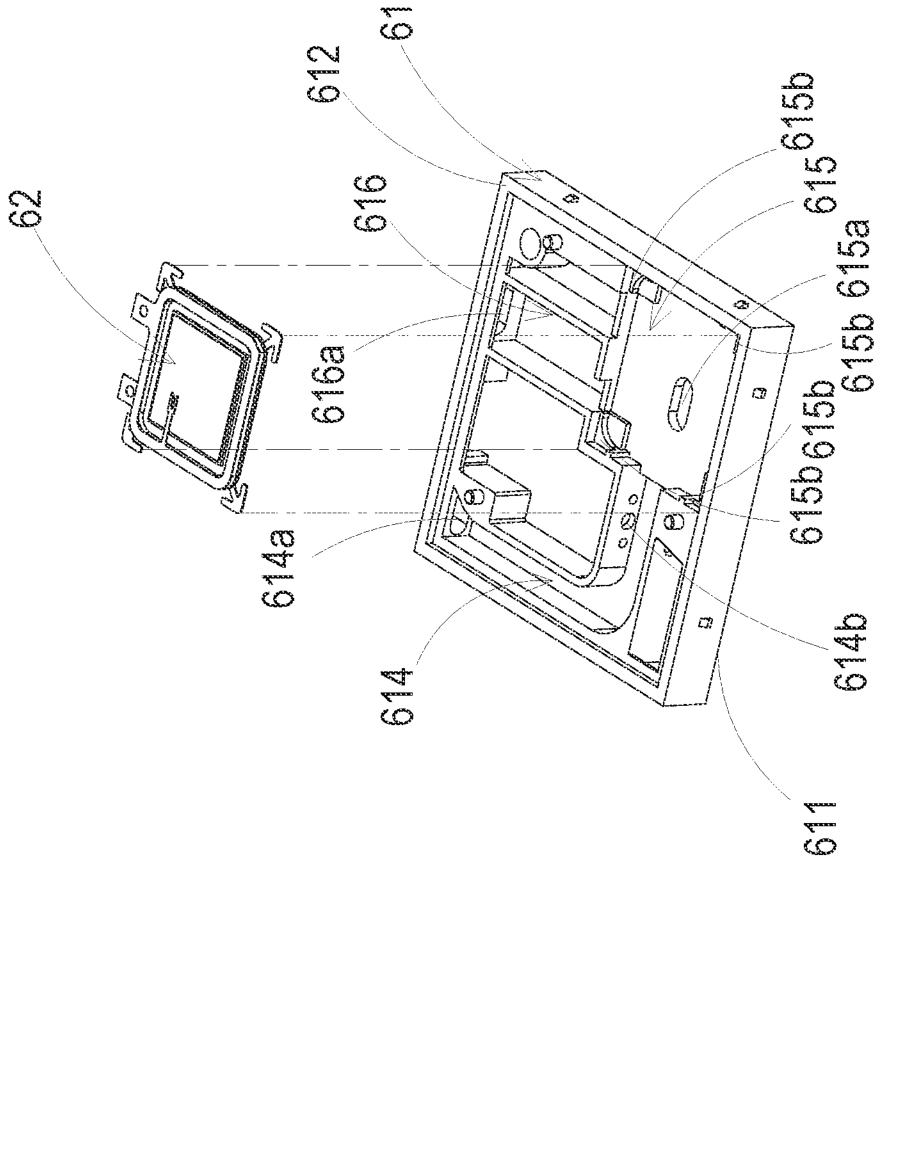
FIG. 6A is a schematic exploded view illustrating the combination of a piezoelectric actuator and the base according to the embodiment of the present disclosure.
Figure 6B:
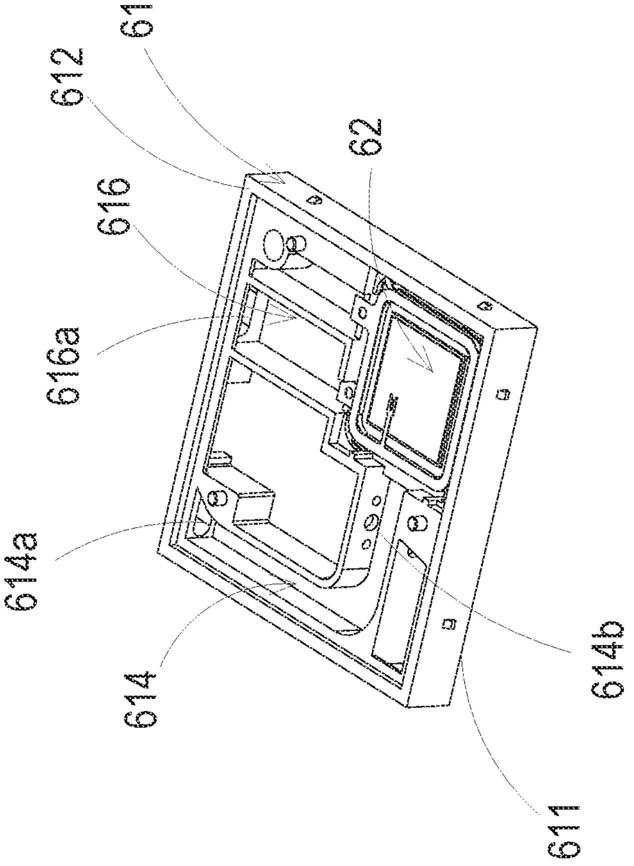
FIG. 6B is a schematic perspective view illustrating the combination of the piezoelectric actuator and the base according to the embodiment of the present disclosure.

As shown in FIG. 5. In the embodiment, the laser component 64 and the particulate sensor 65 are disposed on and electrically connected to the driving circuit board 63 and located within the base 61. In order to clearly describe and illustrate the positions of the laser component 64 and the particulate sensor 65 in the base 61, the driving circuit board 63 is intentionally omitted in FIG. 5. Please refer to FIGS. 3C and 5, the laser component 64 is accommodated in the laser loading region 613 of the base 61, and the particulate sensor 65 is accommodated in the gas-inlet groove 614 of the base 61 and is aligned to the laser component 64. In addition, the laser component 64 is spatially corresponding to the transparent window 614*b*, therefore, a light beam emitted by the laser component 64 passes through the transparent window 614*b* and is irradiated into the gas-inlet groove 614. A light beam path emitted from the laser component 64 passes through the transparent window 614*b* and extends in an orthogonal direction perpendicular to the gas-inlet groove 614.

In the embodiment, a projecting light beam emitted from the laser component 64 passes through the transparent window 614*b* and enters the gas-inlet groove 614 to irradiate the suspended particles contained in the gas passing through the gas-inlet groove 614. When the suspended particles contained in the gas are irradiated and generate scattered light spots, the scattered light spots are received and calculated by the particulate sensor 65 to obtain the gas detection data. In the embodiment, the particulate sensor 65 is a PM2.5 sensor.

Please refer to FIGS. 6A and 6B again. The piezoelectric actuator 62 is accommodated in the gas-guiding-component loading region 615 of the base 61. Preferably but not exclusively, the gas-guiding-component loading region 615 is square and includes four positioning protrusions 615*b* disposed at four corners of the gas-guiding-component loading region 615, respectively. The piezoelectric actuator 62 is disposed in the gas-guiding-component loading region 615 through the four positioning protrusions 615*b*. In addition, the gas-guiding-component loading region 615 is in communication with the gas-inlet groove 614. When the piezoelectric actuator 62 is enabled, the gas in the gas-inlet groove 614 is inhaled by the piezoelectric actuator 62, so that the gas flows into the piezoelectric actuator 62. Furthermore, the gas is transported into the gas-outlet groove 616 through the ventilation hole 615*a* of the gas-guiding-component loading region 615.

Figure 7A:
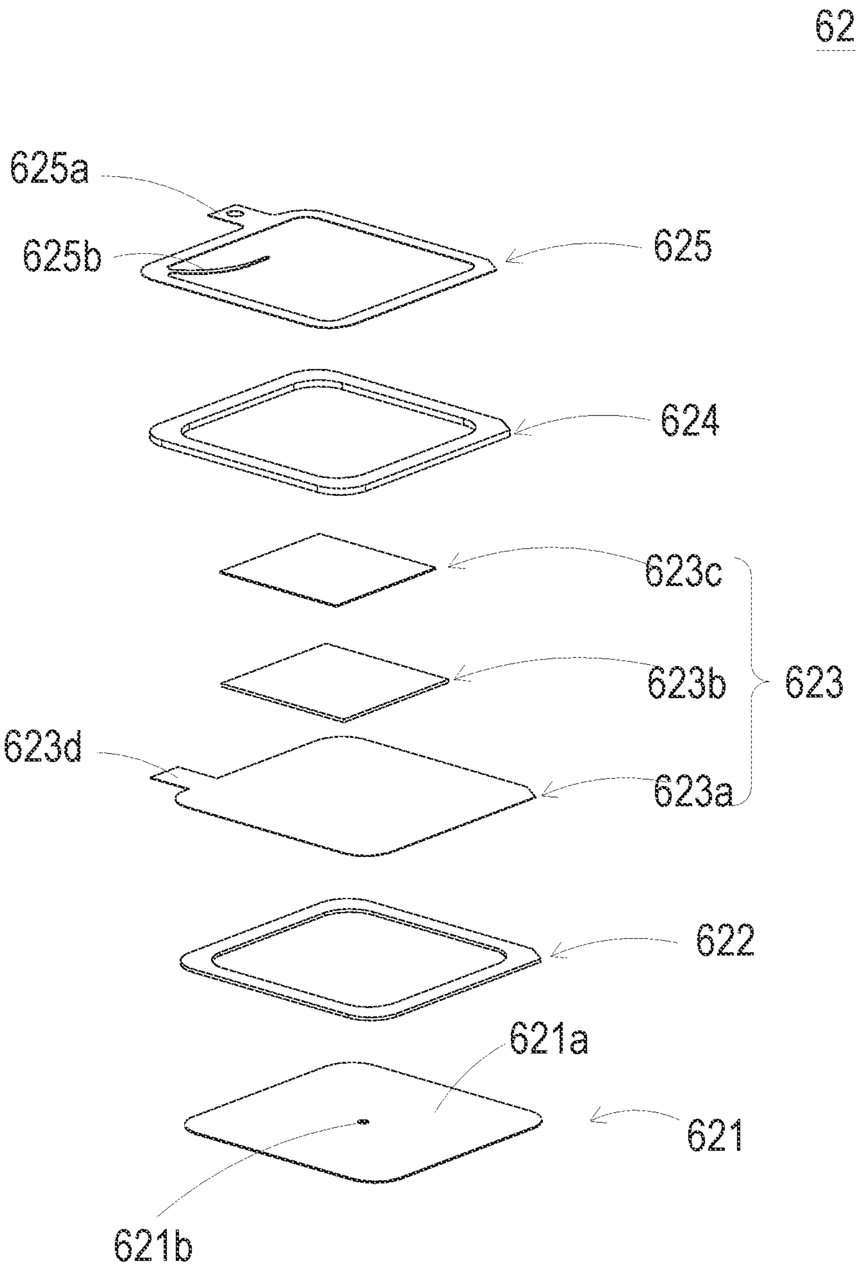
FIG. 7A is a schematic exploded view illustrating the piezoelectric actuator according to the embodiment of the present disclosure.
Figure 7B:
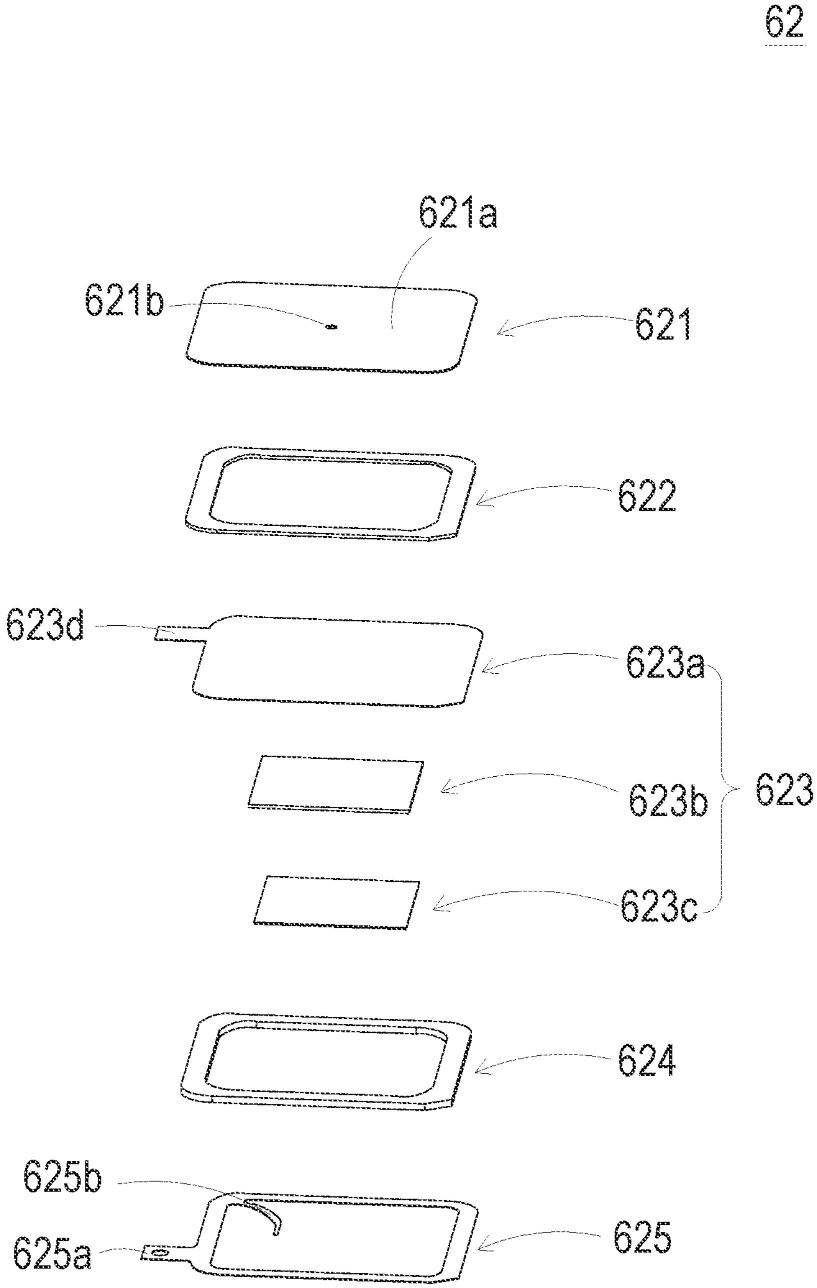
FIG. 7B is a schematic exploded view illustrating the piezoelectric actuator according to the embodiment of the present disclosure and taken from another perspective angle.

Please refer to FIGS. 7A and 7B. In the embodiment, the piezoelectric actuator 62 includes a gas-injection plate 621, a chamber frame 622, an actuator element 623, an insulation frame 624 and a conductive frame 625.

In the embodiment, the gas-injection plate 621 is made by a flexible material and includes a suspension plate 621*a* and a hollow aperture 621*b*. The suspension plate 621*a* is a sheet structure and is permitted to undergo a bending deformation. Preferably but not exclusively, the shape and the size of the suspension plate 621*a* are accommodated in the inner edge of the gas-guiding-component loading region 615, but not limited thereto. Preferably but not exclusively, in the embodiment, the shape of the suspension plate 621*a* is selected from the group consisting of a square, a circle, an ellipse, a triangle and a polygon, but not limited thereto. Moreover, the hollow aperture 621*b* passes through a center of the suspension plate 621*a*, so as to allow the gas to flow therethrough.

In the embodiment, the chamber frame 622 is carried and stacked on the gas-injection plate 621. In addition, the shape of the chamber frame 622 is corresponding to the gas-injection plate 621. The actuator element 623 is carried and stacked on the chamber frame 622. A resonance chamber 626 is collaboratively defined by the actuator element 623, the chamber frame 622 and the suspension plate 621*a* and is formed between the actuator element 623, the chamber frame 622 and the suspension plate 621*a*. The insulation frame 624 is carried and stacked on the actuator element 623 and the appearance of the insulation frame 624 is similar to that of the chamber frame 622. The conductive frame 625 is carried and stacked on the insulation frame 624, and the appearance of the conductive frame 625 is similar to that of the insulation frame 624. In addition, the conductive frame 625 includes a conducting pin 625*a* and a conducting electrode 625*b*. The conducting pin 625*a* is extended outwardly from an outer edge of the conductive frame 625, and the conducting electrode 625*b* is extended inwardly from an inner edge of the conductive frame 625. Moreover, the actuator element 623 further includes a piezoelectric carrying plate 623*a*, an adjusting resonance plate 623*b* and a piezoelectric plate 623*c*. The piezoelectric carrying plate 623*a* is carried and stacked on the chamber frame 622. The adjusting resonance plate 623*b* is carried and stacked on the piezoelectric carrying plate 623*a*. The piezoelectric plate 623*c* is carried and stacked on the adjusting resonance plate 623*b*. The adjusting resonance plate 623*b* and the piezoelectric plate 623*c* are accommodated in the insulation frame 624. The conducting electrode 625*b* of the conductive frame 625 is electrically connected to the piezoelectric plate 623*c*. In the embodiment, the piezoelectric carrying plate 623*a* and the adjusting resonance plate 623*b* are made by a conductive material. The piezoelectric carrying plate 623*a* includes a piezoelectric pin 623*d*. The piezoelectric pin 623*d* and the conducting pin 625*a* are electrically connected to a driving circuit (not shown) of the driving circuit board 63, so as to receive a driving signal, such as a driving frequency and a driving voltage. Through this structure, a circuit is formed by the piezoelectric pin 623*d*, the piezoelectric carrying plate 623*a*, the adjusting resonance plate 623*b*, the piezoelectric plate 623*c*, the conducting electrode 625*b*, the conductive frame 625 and the conducting pin 625*a* for transmitting the driving signal. Moreover, the insulation frame 624 is insulated between the conductive frame 625 and the actuator element 623, so as to avoid the occurrence of a short circuit. Thereby, the driving signal is transmitted to the piezoelectric plate 623*c*. After receiving the driving signal such as the driving frequency and the driving voltage, the piezoelectric plate 623*c* deforms due to the piezoelectric effect, and the piezoelectric carrying plate 623*a* and the adjusting resonance plate 623*b* are further driven to generate the bending deformation in the reciprocating manner.

Furthermore, in the embodiment, the adjusting resonance plate 623*b* is located between the piezoelectric plate 623*c* and the piezoelectric carrying plate 623*a* and served as a cushion between the piezoelectric plate 623*c* and the piezoelectric carrying plate 623*a*. Thereby, the vibration frequency of the piezoelectric carrying plate 623*a* is adjustable. Basically, the thickness of the adjusting resonance plate 623*b* is greater than the thickness of the piezoelectric carrying plate 623*a*, and the vibration frequency of the actuator element 623 can be adjusted by adjusting the thickness of the adjusting resonance plate 623*b*.

Figure 8A:
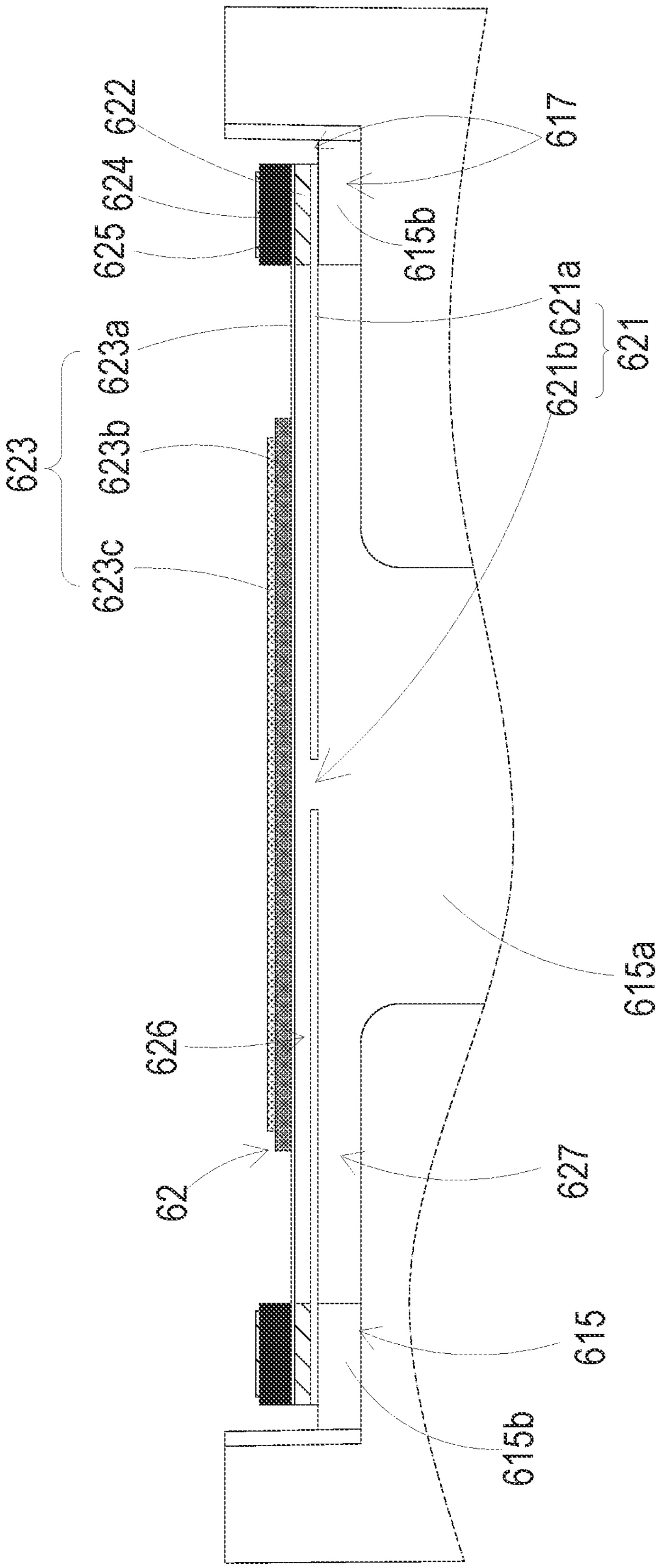
FIG. 8A is a schematic cross-sectional view illustrating the piezoelectric actuator accommodated in a gas-guiding-component loading region according to the embodiment of the present disclosure.
Figure 8B:
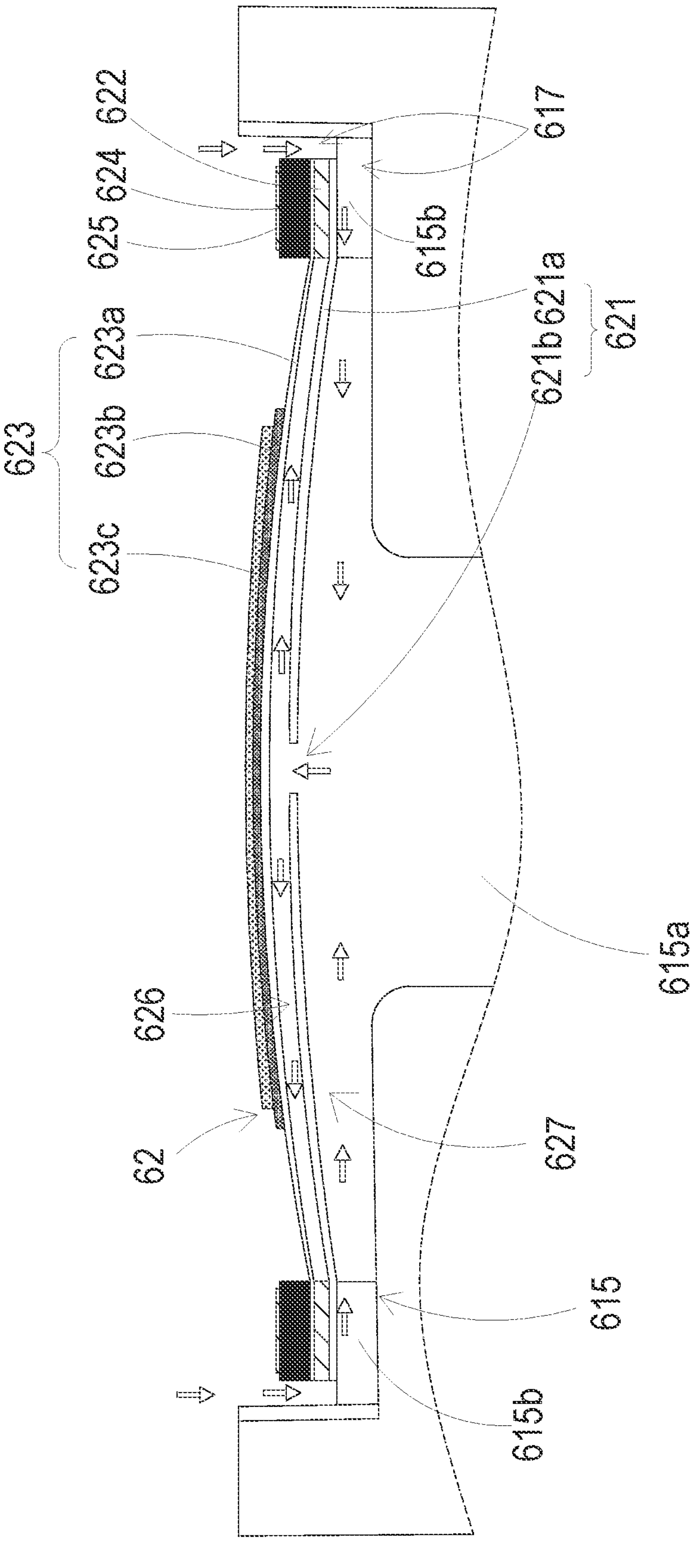
FIGS. 8B and 8C schematically illustrate the actions of the piezoelectric actuator of FIG. 8A.

Please refer to FIGS. 8A and 8B. In the embodiment, the piezoelectric actuator 62 is accommodated on the four positioning protrusions 615*b* of the gas-guiding-component loading region 615. In this circumstance, a plurality of clearances 617 are defined between the suspension plate 621*a* and the positioning protrusions 615*b* of the gas-guiding-component loading region 615, and also between the suspension plate 621*a* and an inner edge of the gas-guiding-component loading region 615 for gas flowing therethrough.

Please refer to FIG. 8A again. In the embodiment, the gas-injection plate 621, the chamber frame 622, the actuator element 623, the insulation frame 624 and the conductive frame 625 are stacked and positioned in the gas-guiding-component loading region 615 sequentially, so that the piezoelectric actuator 62 is supported and positioned in the gas-guiding-component loading region 615. In the embodiment, a flowing chamber 627 is formed between the gas-injection plate 621 and the bottom surface of the gas-guiding-component loading region 615. The flowing chamber 627 is in communication with the resonance chamber 626 between the actuator element 623, the chamber frame 622 and the suspension plate 621*a* through the hollow aperture 621*b* of the gas-injection plate 621. By controlling the vibration frequency of the gas in the resonance chamber 626 to be close to the vibration frequency of the suspension plate 621*a*, the Helmholtz resonance effect is generated between the resonance chamber 626 and the suspension plate 621*a*, so as to improve the efficiency of gas transportation.

Figure 8C:
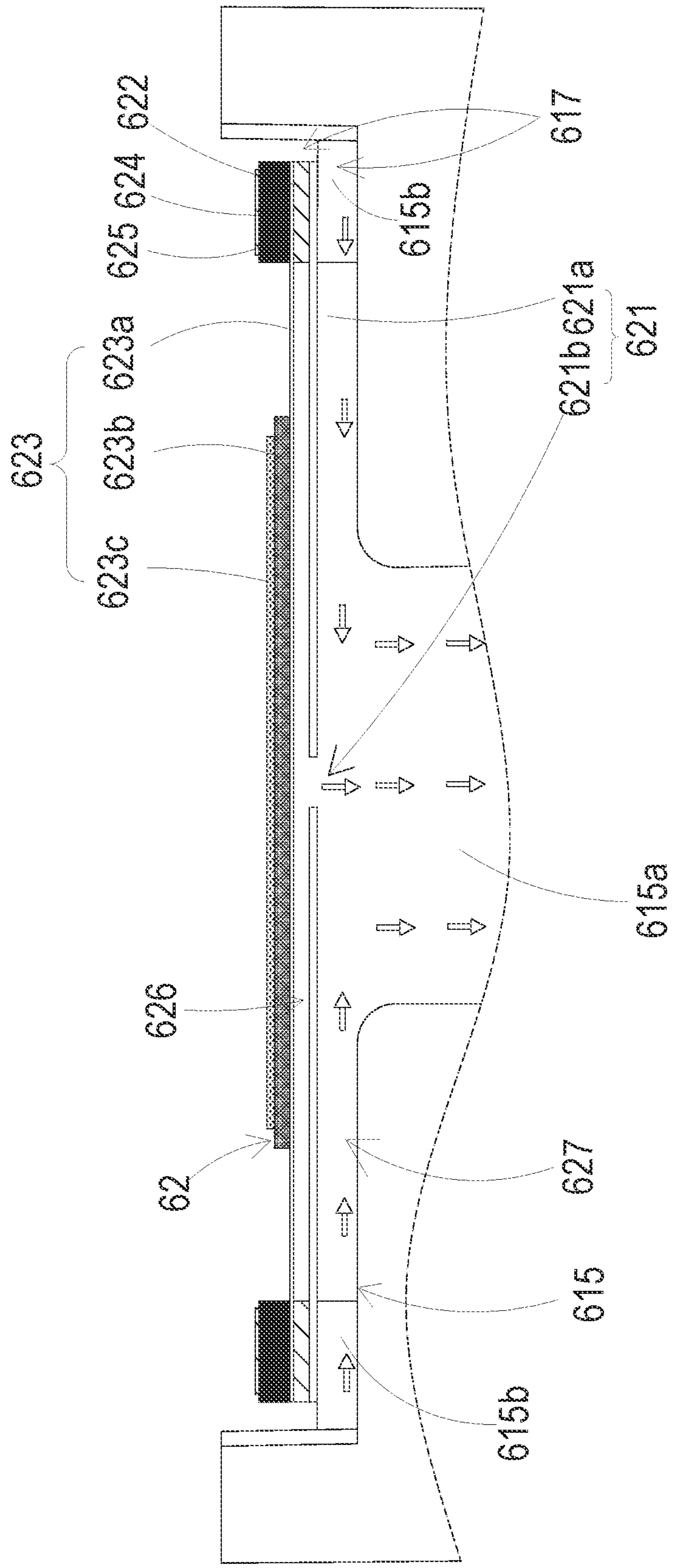

Please refer to FIG. 8B. In the embodiment, when the piezoelectric plate 623*c* is moved away from the bottom surface of the gas-guiding-component loading region 615, the suspension plate 621*a* of the gas-injection plate 621 is driven to move away from the bottom surface of the gas-guiding-component loading region 615 by the piezoelectric plate 623*c*. In that, the volume of the flowing chamber 627 is expanded rapidly, the internal pressure of the flowing chamber 627 is decreased to form a negative pressure, and the gas outside the piezoelectric actuator 62 is inhaled through the clearances 617 and enters the resonance chamber 626 through the hollow aperture 621*b*. Consequently, the pressure in the resonance chamber 626 is increased to generate a pressure gradient. As shown in FIG. 8C, when the suspension plate 621*a* of the gas-injection plate 621 is driven by the piezoelectric plate 623*c* to move toward the bottom surface of the gas-guiding-component loading region 615, the gas in the resonance chamber 626 is discharged out rapidly through the hollow aperture 621*b*, and the gas in the flowing chamber 627 is compressed, thereby the converged gas is quickly and massively ejected out of the flowing chamber 627 under the condition close to an ideal gas state of the Benulli's law. According to the principle of inertia, since the gas pressure inside the resonance chamber 626 is lower than the equilibrium gas pressure after the converged gas is ejected out, the gas is introduced into the resonance chamber 626 again. Therefore, by repeating the above operation steps shown in FIG. 8B and FIG. 8C, the piezoelectric plate 623*c* is driven to generate the bending deformation in a reciprocating manner. Moreover, the vibration frequency of the gas in the resonance chamber 626 is controlled to be close to the vibration frequency of the piezoelectric plate 623*c*, so as to generate the Helmholtz resonance effect to achieve the gas transportation at high speed and in large quantities.

Figure 9A:
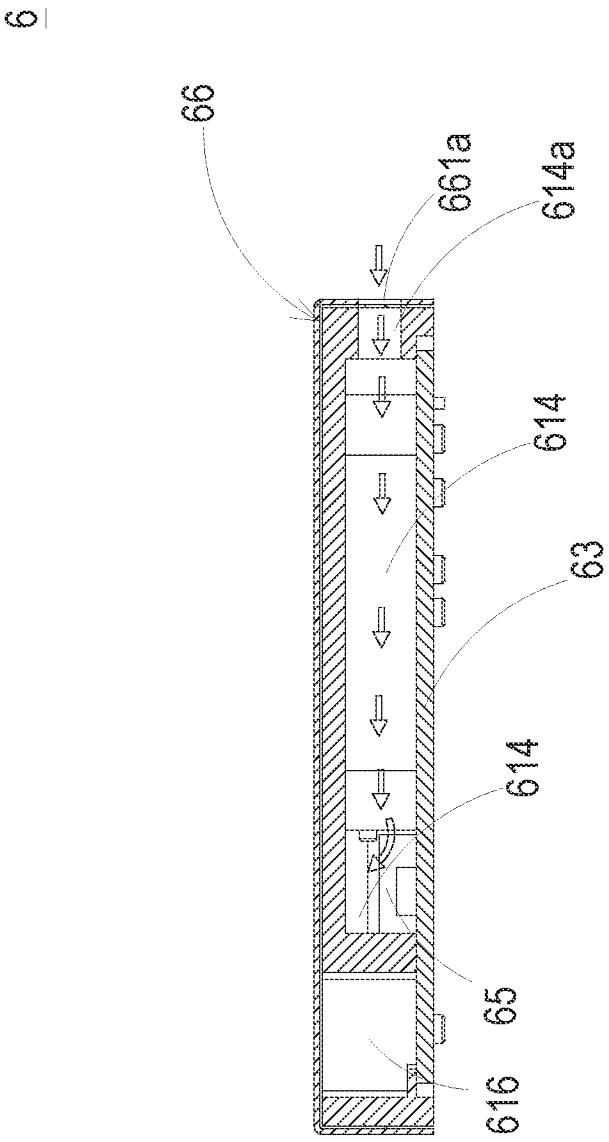
FIGS. 9A to 9C schematically illustrate gas flowing paths of the particle detection module of the present disclosure.
Figure 9B:
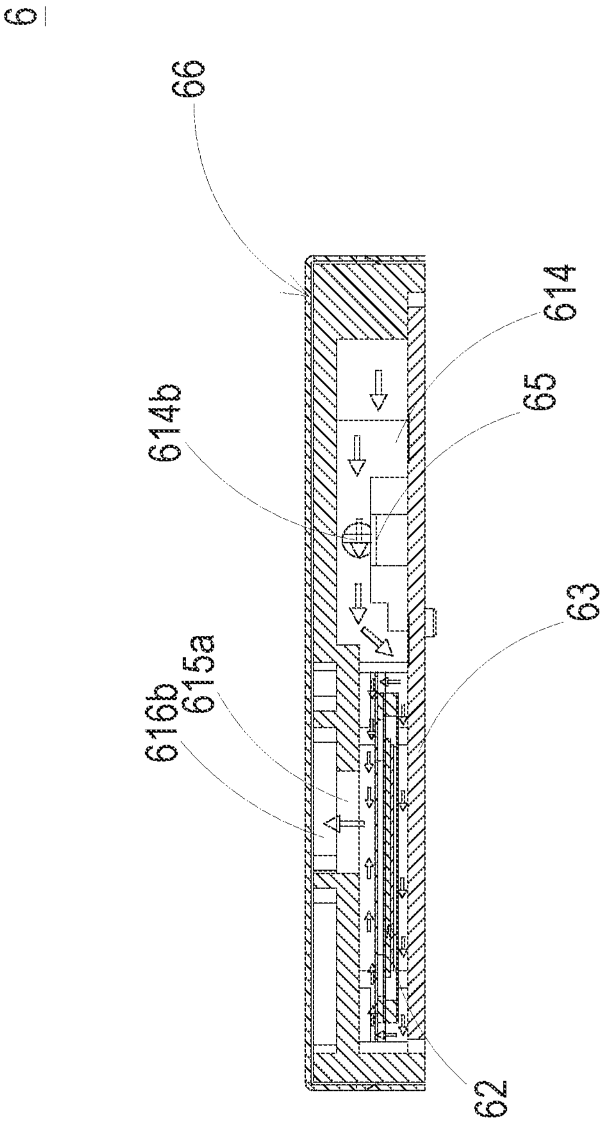
Figure 9C:
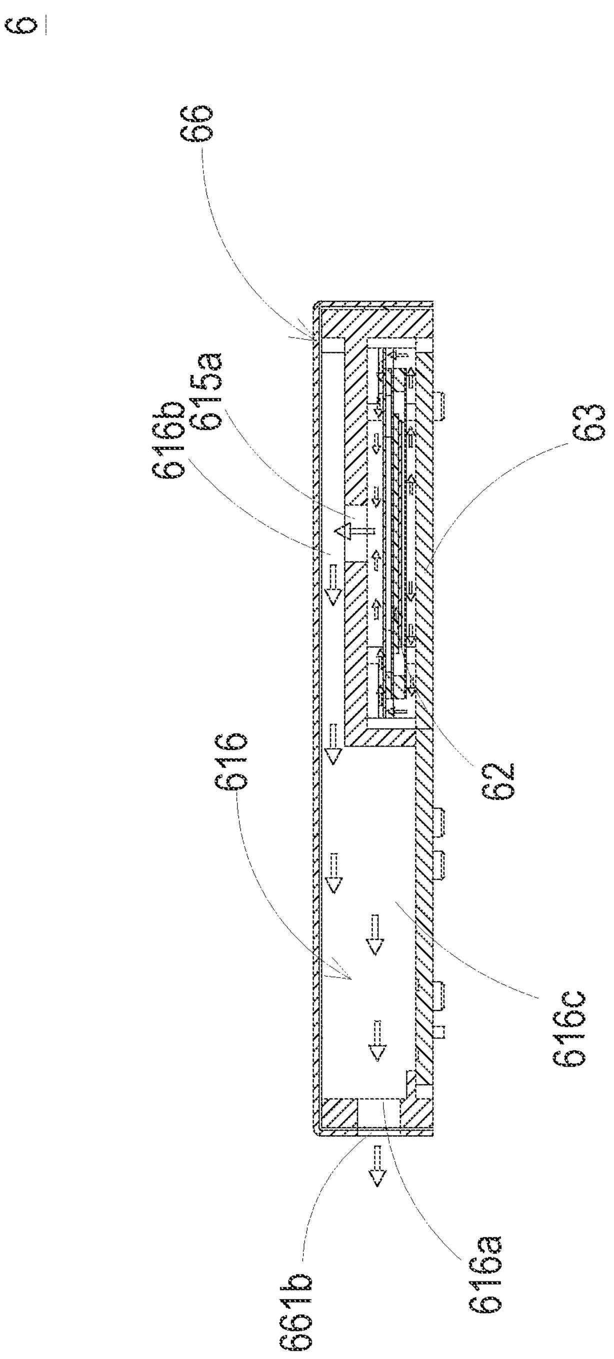

Please refer to FIG. 9A to 9C. The gas is inhaled from the inlet opening 661*a* of the outer cover 66, flows into the gas-inlet groove 614 of the base 61 through the gas-inlet 614*a*, and is transported to the position of the particulate sensor 65. As shown in FIG. 9B, the piezoelectric actuator 62 is enabled continuously to inhale the gas into the inlet path, and facilitate the gas outside the gas detection module to be introduced rapidly, flow stably, and transported above the particulate sensor 65. At this time, a projecting light beam emitted from the laser component 64 passes through the transparent window 614*b* to irritate the suspended particles contained in the gas flowing above the particulate sensor 65 in the gas-inlet groove 614. When the suspended particles contained in the gas are irradiated and generate scattered light spots, the scattered light spots are received and calculated by the particulate sensor 65 for obtaining related information about the sizes and the concentration of the suspended particles contained in the gas. Moreover, the gas above the particulate sensor 65 is continuously driven and transported by the piezoelectric actuator 62, flows into the ventilation hole 615*a* of the gas-guiding-component loading region 615, and is transported to the first section 616*b* of the gas-outlet groove 616. At last, as shown in FIG. 9C, after the gas flows into the first section 616*b* of the gas-outlet groove 616, the gas is continuously transported into the first section 616*b* by the piezoelectric actuator 62, and the gas in the first section 616*b* would be pushed to the second section 616*c*. Finally, the gas is discharged out through the gas-outlet 616*a* and the outlet opening 661*b*.

Figure 10:
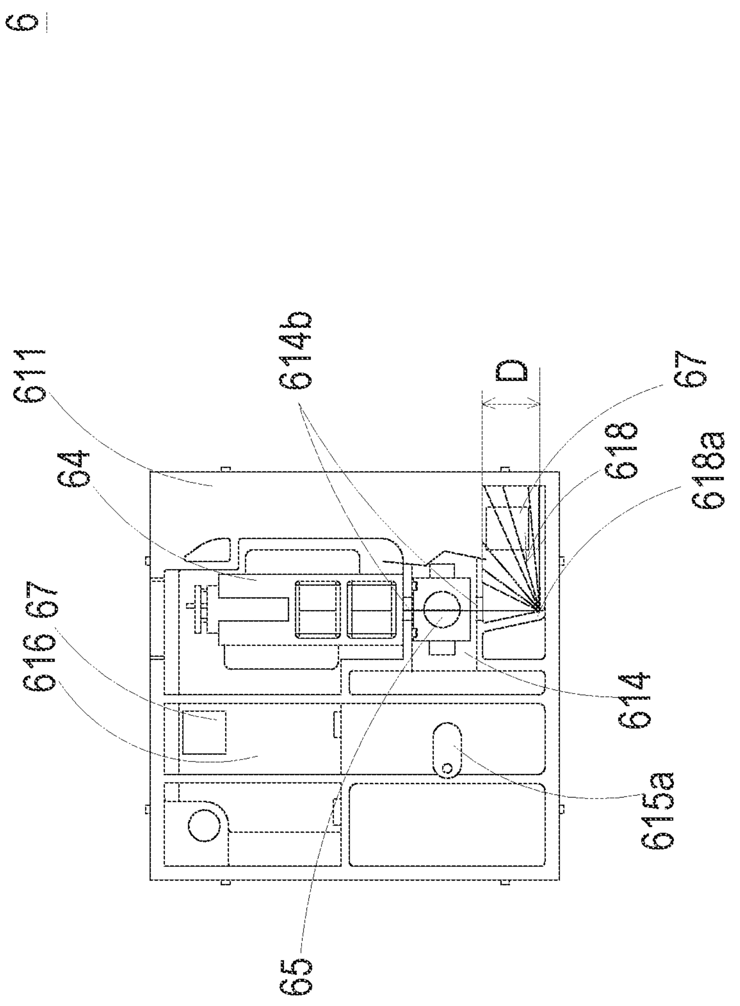
FIG. 10 schematically illustrates a light beam path emitted from the laser component of the particle detection module of the present disclosure.

Notably, as shown in FIG. 10. The base 61 further includes a light trapping region 618. The light trapping region 618 is hollowed out from the first surface 611 to the second surface 612 and spatially corresponds to the laser loading region 613. In the embodiment, the light trapping region 618 is corresponding to the transparent window 614*b* so that the light beam emitted by the laser component 64 is projected into the light trapping region 618. The light trapping region 618 includes a light trapping structure 618*a* having an oblique cone surface. The light trapping structure 618*a* spatially corresponds to the light beam path emitted from the laser component 64. In addition, the projecting light beam emitted from the laser component 64 is reflected into the light trapping region 618 by the oblique cone surface of the light trapping structure 618*a* so as to prevent the projecting light beam from being reflected to the position of the particulate sensor 65. In the embodiment, a light trapping distance D is configured between the transparent window 614*b* and a position where the light trapping structure 618*a* receives the projecting light beam. Preferably but not exclusively, the light trapping distance D is greater than 3 mm. When the light trapping distance D is less than 3 mm, the projecting light beam projected on the light trapping structure 618*a* is easy to be reflected back to the position of the particulate sensor 65 directly due to excessive stray light generated after reflection, and it reduces detection accuracy and results in distortion thereof.

Figure 3A:
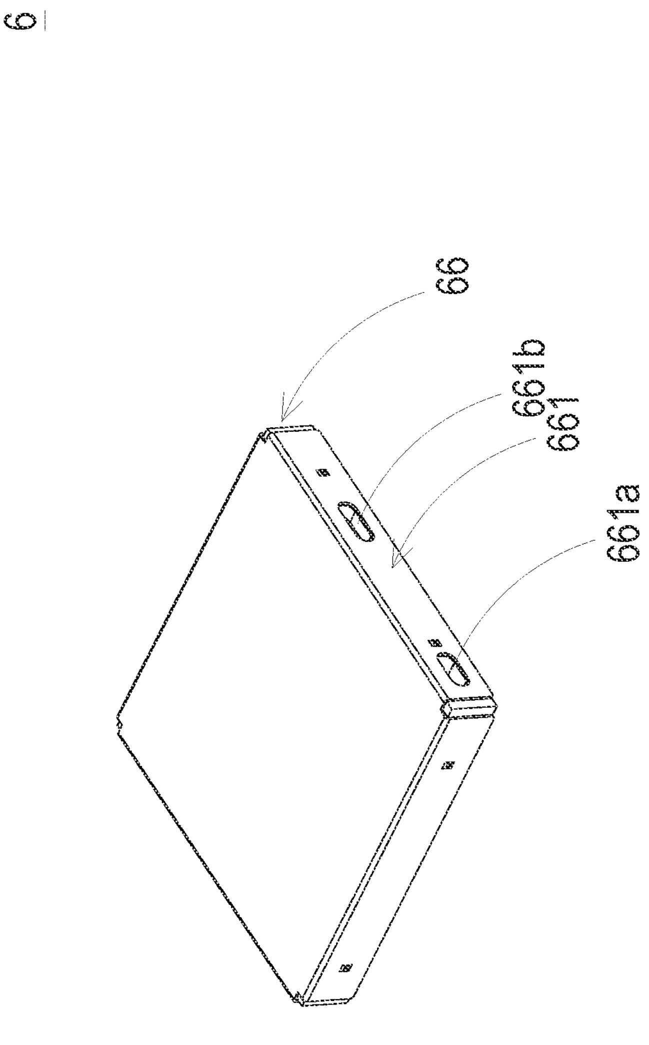
FIG. 3A is a schematic exterior view illustrating a particle detection module of the gas detection device according to the embodiment of the present disclosure.
Figure 3B:
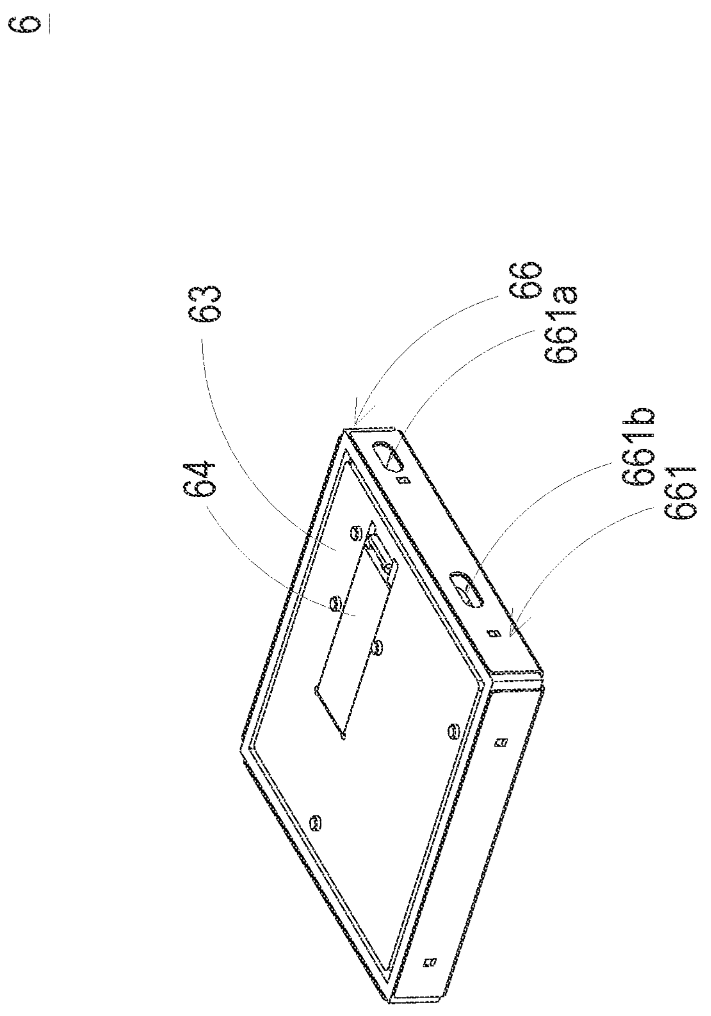
FIG. 3B is a schematic exterior view illustrating the particle detection module according to the embodiment of the present disclosure and taken from another perspective angle.
Figure 3C:
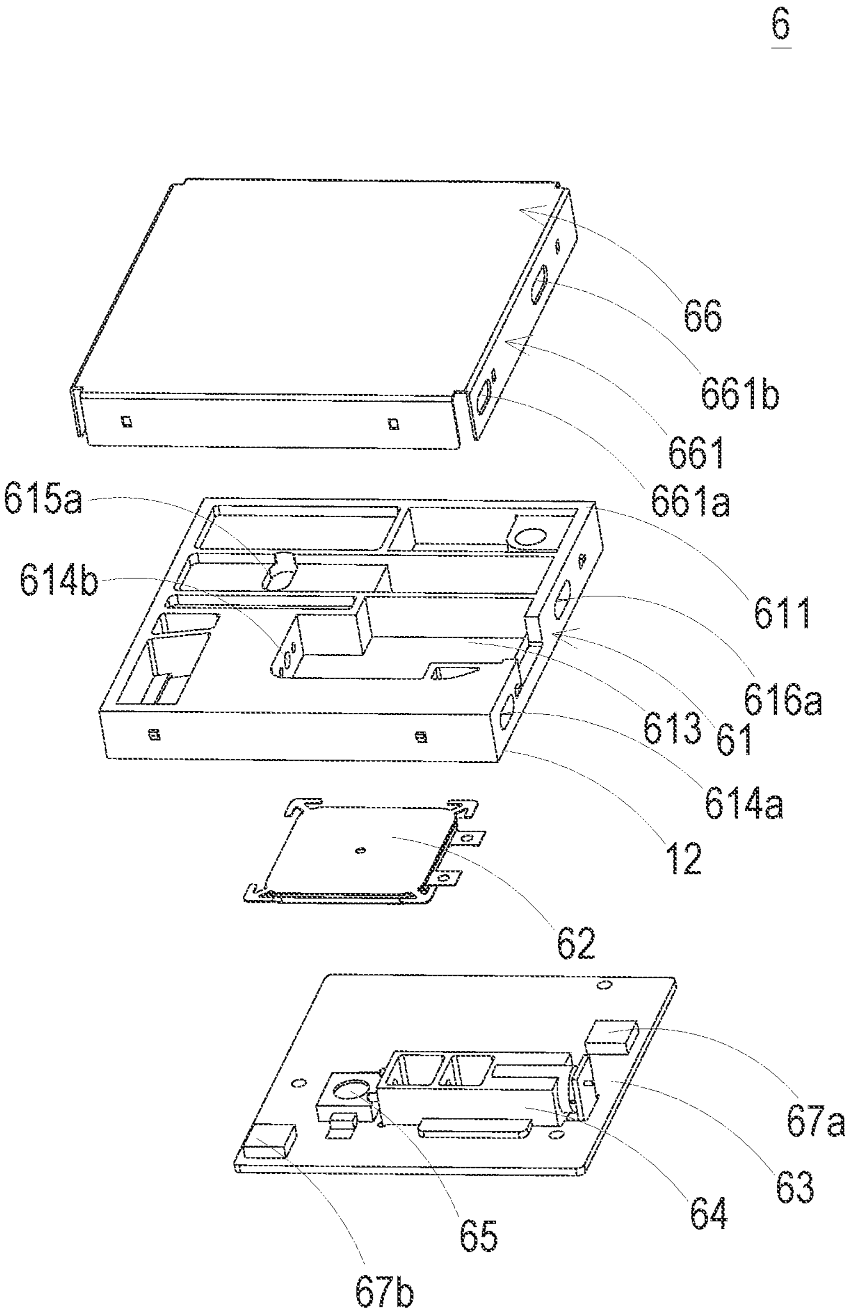
FIG. 3C is a schematic exploded view illustrating the particle detection module according to the embodiment of the present disclosure.

Please refer to FIG. 3C and FIG. 10. The particle detection module 6 of the present disclosure is not only utilized in detection of the suspended particles in the gas, but also further utilized in detection of the characteristics of the introduced gas. Preferably but not exclusively, the gas could be detected is at least one selected from the group consisting of formaldehyde, ammonia, carbon monoxide, carbon dioxide, oxygen, ozone and a combination thereof. In the embodiment, the particle detection module 6 further includes a volatile-organic-compound sensor 67 positioned and disposed on the driving circuit board 63, electrically connected to the driving circuit board 63, and accommodated in the gas-outlet groove 616, so as to detect the gas flowing through the outlet path of the gas-outlet groove 616. Thus, the concentration or the characteristics of volatile organic compounds contained in the gas in the outlet path is detected. In the embodiment, the volatile-organic-compound sensor 67 is accommodated in the light trapping region 618. Thus, the concentration or the characteristics of volatile organic compounds contained in the gas flowing through the inlet path of the gas-inlet groove 614 and transporting into the light trapping region 618 through the transparent window 614*b* could be detected.

In summary, the present disclosure provides a gas detection device, wherein the particle detection module starts detecting the suspended particles (e.g., PM1, PM2.5, or PM10) in the gas, and the temperature and humidity sensor starts detecting the temperature and humidity in the environment. The detected data information of the suspended particles and the temperature and humidity can be transmitted to the control processing board to convert into the communication information, and outputs the communication information to a cloud processing device through the IOT by the networking module. The detected data information can not only be transmitted as warnings or notifications on the indoor display device, but also on the mobile device application (APP). In addition, the detected data information can be compared through intelligent comparison and big data comparison of the cloud processing device. Namely, the cloud processing device sends communication commands to the indoor gas cleaning and exchange filtering devices (such as purifiers, exhaust fans, range hoods, fresh air fans, etc.), so as to effectively remove the indoor air pollution. Consequently, the gas detection device is constructed for detecting gas in an indoor air pollution prevention system, and instantly transmits the air quality information to the system, so as to achieve a clean and safe breathing gas state. The present disclosure includes the industrial applicability and the inventive steps.

What is claimed is:

1. A gas detection device, comprising:

a housing including an upper housing and a lower housing, wherein a plurality of vents are arranged on an side edge of the lower housing, a lug hole is arranged on a lower side of the lower housing, and a recessed groove is formed on a bottom surface of the lower housing;

an external connector pivotally connected to the lower housing, wherein when not in use, the external connector is folded and hidden in the recessed groove without protruding, and when in use, the external connector is rotated out the recessed groove to be exposed out of the lower case, and connected to an external power supply;

a power converter electrically connected to the external connector, and configured to convert the external power supply into a DC power;

a control processing board electrically connected to the power converter for providing an activation power supply, and configured to receiver and process a plurality of data information to convert the data information into a communication information;

a networking module disposed on a side of the upper housing, and integrally packaged on the control processing board to form an integrated circuit, and configured to receive and output the communication information processed by the control processing board;

a particle detection module disposed and positioned on an other side of the bottom surface of the lower housing, and arranged on the control processing board on an opposite side of the control processing board from the networking module, wherein the particle detection module is electrically connected to the control processing board through a first flexible band to detect gas and acquire the data information of the gas, transmits the data information to the control processing board to convert the data information into the communication information, and outputs the communication information through the networking module; and a temperature and humidity sensor disposed on a side of the lower housing, and electrically connected to the control processing board through a second flexible band for detecting temperature and humidity, and acquiring the data information of the temperature and humidity, wherein the data information is transmitted to the control processing board to convert the data information into the communication information, and the communication information is outputted through the networking module.

2. The gas detection device according to claim 1, wherein the external connector is one selected from the group consisting of a power connector, a USB port, a mini-USB port, a Micro-USB port and a Type-C USB port.

3. The gas detection device according to claim 1, wherein when the external connector is plugged into the external power supply, a locking element passes through the lug hole and is locked into a socket, so as to position the entire gas detection device.

4. The gas detection device according to claim 1, wherein the networking module is a cloud computing service wireless network communication module, and is disposed on the side of the upper housing, which is exposed outside the gas detection device so that the networking module can receive or send communication signals while being shielded by the control processing board, which prevents interference to the communication signals.

5. The gas detection device according to claim 1, wherein the particle detection module detects the gas introduced formfrom the plurality of vents of the housing, and the particle detection module structure comprises:

a base comprising:

a first surface;

a second surface opposite to the first surface;

a laser loading region hollowed out from the first surface to the second surface;

a gas-inlet groove concavely formed from the second surface and disposed adjacent to the laser loading region, wherein the gas-inlet groove comprises a gas-inlet and two lateral walls, the gas-inlet is in communication with an environment outside the base, and a transparent window is opened on the two lateral walls and is in communication with the laser loading region;

a gas-guiding-component loading region concavely formed from the second surface and in communication with the gas-inlet groove, wherein a ventilation hole penetrates a bottom surface of the gas-guiding-component loading region; and a gas-outlet groove concavely formed from the first surface, spatially corresponding to the bottom surface of the gas-guiding-component loading region, and hollowed out from the first surface to the second surface in a region where the first surface is not aligned with the gas- guiding-component loading region, wherein the gas-outlet groove is in communication with the ventilation hole, and a gas-outlet is disposed in the gas-outlet groove and in communication with the environment outside the base;

a piezoelectric actuator accommodated in the gas-guiding-component loading region;

a driving circuit board covering and attached to the second surface of the base;

a laser component positioned and disposed on the driving circuit board, electrically connected to the driving circuit board, and accommodated in the laser loading region, wherein a light beam path emitted from the laser component passes through the transparent window and extends in a direction perpendicular to the gas-inlet groove, thereby forming an orthogonal direction with the gas-inlet groove;

a particulate sensor positioned and disposed on the driving circuit board, electrically connected to the driving circuit board, and disposed at an orthogonal position where the gas-inlet groove intersects the light beam path of the laser component in the orthogonal direction, so that suspended particles passing through the gas-inlet groove and irradiated by a projecting light beam emitted from the laser component are detected; and an outer cover covering the first surface of the base and comprising a side plate, wherein the side plate has an inlet opening spatially corresponding to the gas-inlet and an outlet opening spatially corresponding to the gas-outlet, respectively, wherein the first surface of the base is covered with the outer cover, and the second surface of the base is covered with the driving circuit board, so that an inlet path is defined by the gas-inlet groove, and an outlet path is defined by the gas-outlet groove, so that the gas is inhaled from the environment outside base by the piezoelectric actuator, transported into the inlet path defined by the gas-inlet groove through the inlet opening, and passes through the particulate sensor to detect the concentration of the suspended particles contained in the gas, and the gas transported through the piezoelectric actuator is transported out of the outlet path defined by the gas-outlet groove through the ventilation hole and then discharged through the outlet opening.

6. The gas detection device according to claim 5, wherein the gas-guiding-component loading region has four positioning protrusions disposed at four corners thereof for accommodating and positioning the piezoelectric actuator.

7. The gas detection device according to claim 6, wherein the piezoelectric actuator comprises:

a gas-injection plate comprising a suspension plate and a hollow aperture, wherein the suspension plate is permitted to undergo a bending deformation, and the hollow aperture is formed at a center of the suspension plate, the piezoelectric actuator is accommodated on the four positioning protrusions of the gas-guiding-component loading region, so that a flowing chamber is formed between the gas-injection plate and a bottom surface of the gas-guiding-component loading region, and a plurality of clearances are defined between the suspension plate and the positioning protrusions of the gas-guiding-component loading region, and also between the suspension plate and an inner edge of the gas-guiding-component loading region for gas flowing therethrough;

a chamber frame carried and stacked on the suspension plate;

an actuator element carried and stacked on the chamber frame for being driven in response to an applied voltage to undergo the bending deformation in a reciprocating manner;

an insulation frame carried and stacked on the actuator element; and a conductive frame carried and stacked on the insulation frame, wherein a resonance chamber is formed among the actuator element, the chamber frame and the suspension plate, when the actuator element is enabled to drive the gas-injection plate to move in resonance, the suspension plate of the gas-injection plate is driven to generate the bending deformation in a reciprocating manner, the gas is inhaled through the vacant space, flows into the flowing chamber, and is discharged out, so as to achieve gas transportation.

8. The gas detection device according to claim 6, wherein the actuator element comprises:

a piezoelectric carrying plate stacked on the chamber frame;

an adjusting resonance plate stacked on the piezoelectric carrying plate; and a piezoelectric plate stacked on the adjusting resonance plate, wherein the piezoelectric plate is configured to receive the applied voltage and drive the piezoelectric carrying plate and the adjusting resonance plate to generate the bending deformation in the reciprocating manner.

9. The gas detection device according to claim 5, wherein the base comprises a light trapping region hollowed out from the first surface to the second surface and spatially corresponding to the laser loading region, wherein the light trapping region comprises a light trapping structure having an oblique cone surface and spatially corresponding to the light beam path.

10. The gas detection device according to claim 9, wherein a light trapping distance is configured between the transparent window and a position where the light trapping structure receives the projecting light beam.

11. The gas detection device according to claim 10, wherein the light trapping distance is greater than 3 mm.

12. The gas detection device according to claim 9, wherein the particle detection module structure further comprising a volatile-organic-compound sensor.

13. The gas detection device according to claim 12, wherein the volatile-organic-compound sensor is positioned and disposed on the driving circuit board, electrically connected to the driving circuit board, and accommodated in the gas-outlet groove, so as to detect the gas flowing through the outlet path of the gas-outlet groove.

14. The gas detection device according to claim 12, wherein the volatile-organic-compound sensor is positioned and disposed on the driving circuit board, electrically connected to the driving circuit board, and accommodated in the light trapping region, so as to detect the gas flowing through the inlet path of the gas-inlet groove and transported into the light trapping region through the transparent window.

15. The gas detection device according to claim 5, wherein the particulate sensor is a PM2.5 sensor.

* * * * *